(12) United States Patent
Gutman et al.

(10) Patent No.: US 6,555,665 B1
(45) Date of Patent: Apr. 29, 2003

US006555665B1

(54) GLYCOSIDATION OF 4,5-EPOXYMORPHINAN-6-OLS

(75) Inventors: Arie Gutman, Haifa (IL); Genadi Nisnevitch, Nesher (IL); Lev Yudovitch, Haifa (IL); Igor Rochman, Kyriat Yam (IL)

(73) Assignee: Cenes Limited, Cambridge (GB)

( * ) Notice: Subject to any disclaimer, the term of this patent is extended or adjusted under 35 U.S.C. 154(b) by 0 days.

(21) Appl. No.: 09/601,358

(22) PCT Filed: Feb. 2, 1999

(86) PCT No.: PCT/GB99/00336

§ 371 (c)(1),
(2), (4) Date: Sep. 15, 2000

(87) PCT Pub. No.: WO99/38876

PCT Pub. Date: Aug. 5, 1999

(30) Foreign Application Priority Data

| Feb. 2, 1998 | (IL) | 123149 |
| Aug. 4, 1998 | (IL) | 125652 |
| Jan. 15, 1999 | (GB) | 9900831 |

(51) Int. Cl.$^7$ ............. C07H 15/00; C07H 15/24; C07H 17/00
(52) U.S. Cl. .............. 536/17.4; 536/18.1; 536/18.5; 536/119
(58) Field of Search ............ 536/17.4, 18.1, 536/18.5, 119

(56) References Cited

U.S. PATENT DOCUMENTS 5,621,087 A * 4/1997 Scheinmann et al.

FOREIGN PATENT DOCUMENTS

| WO | WO 93/03051 | 2/1993 |
| WO | WO 93/05057 | 3/1993 |

OTHER PUBLICATIONS

Berrang, B., et al., *Synthesis*, 1997, p. 1165.
Osborne, R. et al. "Analgesic Activity of Morphine–6–Glucuronide," The Lancet, vol. I, Apr. 9, 1988, p. 828.
Osborne, R. et al. "Analgesic Activity of Morphine–6–Glucuronide," Br. J. Clin. Pharm., vol. 34, Aug. 1992, pp. 130–138.
Frances, B. et al. "Analgesic Activity of Morphine–6–Glucuronide," J. Pharm. Exp. Ther., vol. 262, Jul. 1992, pp. 25–31.

\* cited by examiner

*Primary Examiner*—Samuel Barts
*Assistant Examiner*—Michael C. Henry

(57) ABSTRACT

Glycosidation of 4,5-Epoxymorphinan-6-ols with a Thioglycoside as a glycoside donor is disclosed. The process comprises reacting a 4,5-Epoxymorphinan-6-ol and a Thioglycoside in the presence of a thiophilic promoter under conditions capable of forming 4,5-Epoxymorphinan-6-glycosides. This novel approach was used for preparation of pharmaceutically important 4,5-Epoxymorphinan-6-β-D-glucuronides. The process provides both high stereoselectivity and high yields.

18 Claims, No Drawings

GLYCOSIDATION OF 4,5-EPOXYMORPHINAN-6-OLS

BACKGROUND OF THE INVENTION

The present invention relates to glycosidation of 4,5-Epoxymorphinan-6-ols using Thioglycosides as glycoside donors. This approach is particularly useful for preparation of protected 4,5-Epoxymorphinan-6-β-D-glucuronides of formula [1]

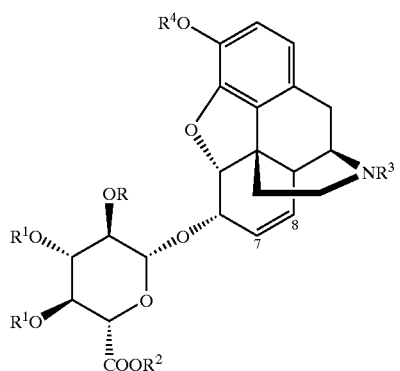

[1]

wherein:

position 7 and 8 can be olefin as shown or dihydro adduct;

R is acyl, alkoxycarbonyl, aralkoxycarbonyl, haloalkoxycarbonyl, vinyloxycarbonyl, allyloxycarbonyl;

$R^1$ is alkyl, arylmethyl, acyl, alkoxycarbonyl, aralkoxycarbonyl, haloalkoxycarbonyl, vinyloxycarbonyl, allyloxycarbonyl;

$R^2$ is alkyl, haloalkyl, aralkyl;

$R^3$ is alkyl, arylmethyl, allyl, cyclopropylmethyl, cyclobutylmethyl, hydrogen, acyl, alkoxycarbonyl, aralkoxycarbonyl, haloalkoxycarbonyl, vinyloxycarbonyl, allyloxycarbonyl;

$R^4$ is alkyl, arylmethyl, 2-(4-morpholinyl)ethyl, acyl, alkoxycarbonyl, aralkoxycarbonyl, haloalkoxycarbonyl, vinyloxycarbonyl, allyloxycarbonyl.

Since it was established that Morphine-6-β-D-glucuronide (M6G) [1a] is not only a metabolite of Morphine [5] but also has greater analgesic activity[1], substantial amounts have been required for clinical trials and evaluation. According to recent publications the morphine metabolite M6G is a more effective and longer lasting analgesic drug than Morphine itself and has fewer side effects.[2]

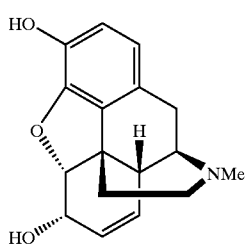

[5]

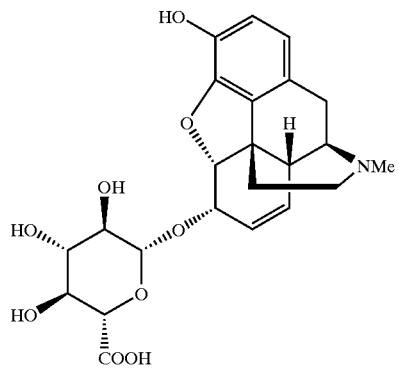

[1a]

Unfortunately, morphine is also metabolized to Morphine-3-glucuronide (M3G) [6], a compound which antagonizes the analgesic effect of Morphine. Since M3G is formed in greater abundance than M6G, there is much interest in using the latter, rather than Morphine, as a pain killing drug.[3]

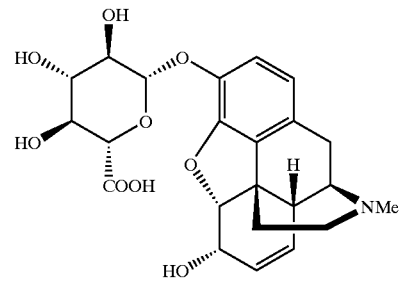

[6]

The traditional approach to glycosidation of 4,5-Epoxymorphinan-6-ols explores haloglycosides as glycoside donors and the Koenings-Knorr procedure for the activation of haloglycosides (Berrang, B. et al., Synthesis, 1997, 1165 and references cited therein). The main drawbacks of this approach are: low stability of haloglycosides, heterogenic reaction media that make industrial scale-up very tedious, with low and unstable yields, use of heavy metals. Another more recent approach, described by F. Sheinmann et al. (U.S. Pat. No. 5,621,087), describes use of trichloroacetimidates as glycoside donors. The main disadvantages of this approach are: the tedious methods for preparation of the starting trichloroacetimidates; relatively low yields in the glycosidation reaction; difficult purification of the desired product from the reaction mixture.

These methods have, therefore, serious drawbacks for producing bulk material to be used as a pharmaceutical drug. A desirable goal, met by the present invention, has been to devise synthetic methods which avoid toxic and/or expensive reagents, and which cleanly produce the desired products, avoiding tedious and expensive purification steps.

SUMMARY OF THE INVENTION

Glycosidation of 4,5-Epoxymorphinan-6-ols with Thioglycosides as a glycoside donors is disclosed. The process comprises reacting 4,5-Epoxymorphinan-6-ols and Thioglycosides in the presence of thiophilic promoters under conditions capable of forming 4,5-Epoxymorphinan-6-glycosides. This novel approach was used for preparation of protected 4,5-Epoxymorphinan-6-β-D-glucuronides. The process provides both high stereo-selectivity and high yields.

DETAILED DESCRIPTION OF THE INVENTION

The present invention relates to the use of Thioglycosides as glycoside donors for glycosidation of 4,5-Epoxymorphinan-6-ols.

This novel approach has several advantages:

Thioglycosides can be prepared according to known methods starting from inexpensive and commercially available raw materials.

Thioglycosides have high thermal and chemical stability.

Reagents used for the Thioglycoside activation are not toxic and not expensive.

Although any 4,5-Epoxymorphinan-6-ols, suitable for this glycosylation, can be used, preferably compounds of formula [3] are used.

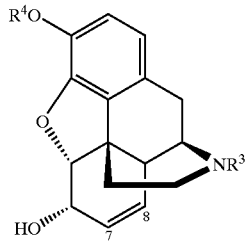

[3]

wherein:

position 7 and 8 can be olefin as shown or dihydro adduct;

$R^3$ and $R^4$ are as previously defined

More preferably, said 4,5-Epoxymorphinanes are selected from 3-O-Acylmorphine, 3-O-Acylnormorphine, 3-O-Acylnalbuphine, 3-O-Acylnalorphine, 3-O-Acyldihydromorphine, 3-O-Benzylmorphine, 3-O-Benzyldihydromorphine, N,O³-Dibenzylnormorphine, Codeine, Ethylmorphine, Dihydrocodeine, Pholcodine, 3-O-Alkoxycarbonylmorphine, 3-O-Benzyloxycarbonylmorphine, N,O³-Bis(benzyloxycarbonyl)normorphine.

Although any Thioglyoside may be used, it is preferred that Thioglycosides of formula [2] are used.

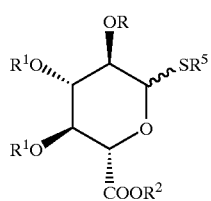

[2]

wherein

R, $R^1$ and $R^2$ are as previously defined $R^5$ is alkyl or aryl.

More preferably the Thioglycosides of the present invention are selected from the compounds of formula [12].

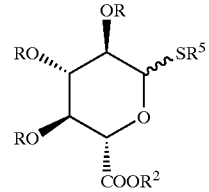

[12]

wherein
R, $R^2$ and $R^5$ are as previously defined;

Most preferably Thioglycosides of formula [11] are used.

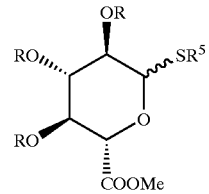

[11]

wherein
R and $R^5$ are as previously defined.

Thiophilic promoters used in said glycosidation could be selected from halonium ion source, Dimethyl(methylthio)sulfonium triflate or tetrafluoroborate, Methyl triflate or fluorosulfonate.

The Halonium ion source used in the present invention is a mixture of N-Halosuccinimide and acid, or Iodonium dicollidine perchlorate (IDCP). The said N-Halosuccinimide is preferably selected from N-Iodosuccinimide (NIS) or N-Bromosuccinimide (NBS).

The said acids may be selected from triflic acid, trimethylsilyl triflate, silver triflate or tetrafluoroborate or trifluoromethanesulfonic acid.

Most preferably the said thiophilic promoters are a mixture of NIS and triflic acid, or Dimethyl(methylthio)sulfonium triflate.

Preferably the said reaction occurs in the presence of reaction-inert solvents.

Any reaction-inert solvent may be used. As used above and elsewhere herein, the expression "reaction-inert solvent" refers to a solvent which does not react or decompose with starting materials, reagents, intermediates or products in a manner which adversely affects the yield of the desired product. In general, the solvent can comprise a single entity, or contain multiple components.

Preferably the said reaction-inert solvents are non-protic and are selected from Dichloromethane, Chloroform, 1,2-Dichloroethane, Ether, Acetonitrile, or mixture thereof. Diethyl ether or ethyl acetate may alternatively or additionally be used as a non-protic reaction-inert solvent. Dichloromethane is an especially preferred solvent.

It may be also preferred to conduct the said coupling reaction in the presence of additives to buffer or to activate the thiophilic promoter. The above additives may be selected from molecular sieves, tertiary amines, tetraalkylureas, organic and inorganic acids and salts.

Preferably about 1 equivalent to about 2 equivalents of the Thioglycoside is used. It is specially preferred that about 1 equivalent to about 1.5 equivalents of Thioglycoside is used. The said 4,5-Epoxymorphinanes may be used as an individual compounds or alternatively as corresponding salts thereof or complexes.

Any environment or conditions (e.g. temperature, time, solvent) suitable for the glycosidation reaction may be used. However, it is preferred that the reaction occurs at a temperature of about −50° C. to about 100° C. and preferably from about −20° C. to 20° C. This reaction is conveniently carried out at about 0.5 to about 3 atmospheres.

This invention makes a significant advance in the chemistry of 4,5-Epoxymorphinan-6-ols by providing an efficient method for preparation of a large number of known and new 4,5-Epoxymorphinan-6-glycosides.

Particularly, protected 4,5-Epoxymorphinan-6-β-D-glucuronides [1] could be obtained by glycosidation of 4,5-Epoxymorphinan-6-ols of formula [3] or salts thereof or complexes containing thereof

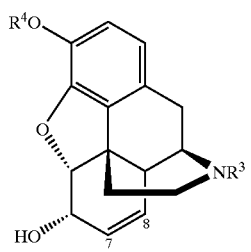

wherein:
position 7 and 8 can be olefin as shown or dihydro adduct;
$R^3$ and $R^4$ are as previously defined.
with thioglycoside of the formula [2]

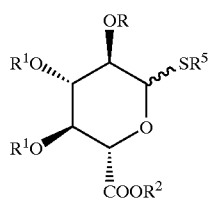

wherein
R, $R^1$, $R^2$ and $R^5$ are as previously defined.
under conditions capable of forming said protected 4,5-Epoxymorphinan-6-β-D-glucuronides [1] or salts thereof or complexes containing thereof More preferably, protected N-Methy-4,5-epoxymorphinan-6-β-D-glucuronides of formula [4] or salts thereof or complexes containing thereof could be obtained by glycosidation of N-Methyl-4,5-epoxymorphinan-6-ol of formula [3a] with Thioglycosides of formula [12]

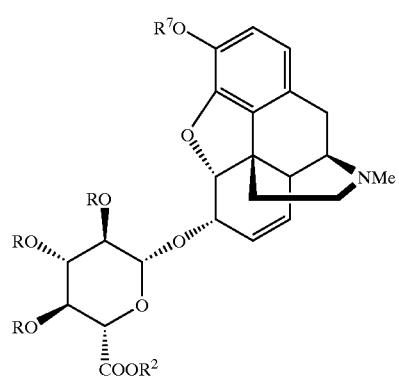

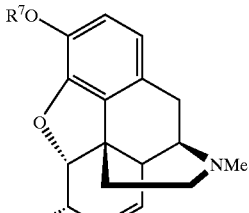

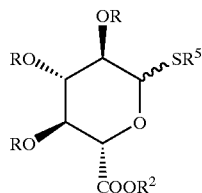

wherein
R, $R^2$, $R^5$ and $R^7$ are as previously defined.
Said protected N-Methyl-4,5-epoxymorphinan-6-β-D-glucuronide of formula [4] could be important intermediates for the synthesis of Morphine-6-β-D-glucuronide (M6G).

It should be understood that the invention is not limited to the particular embodiments shown and described herein, but that various changes and modifications may be made without departing from the spirit and scope of this novel concept as defined by the following claims.

EXAMPLE 1

Preparation of Methyl (3-O-Benzoylmorphin-6-yl-2',3',4'-Tri-O-isobutyryl-β-D-glucopyranosid)uronate of Formula [8]

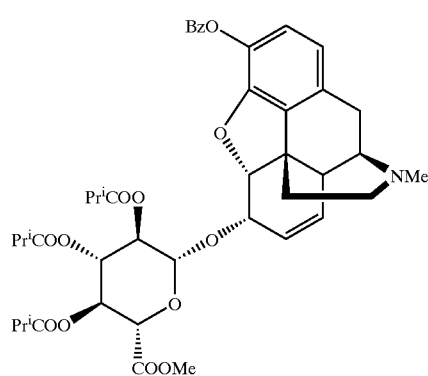

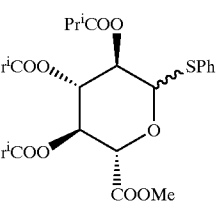

A suspension of Thioglycoside [9] (17.6 g, 34.5 mmol), freshly prepared, vacuum-dried 3-O-Benzoylmorphine (8.9 g, 23 mmol) and 3Å Molecular Sieves (30.0 g) in 30 mL Dichloromethane was stirred at room temperature for 30 min and cooled to −10° C. by an ice-salt bath. Trifluoromethanesulfonic acid (TfOH) (5.0 g, 33.5 mmol) was added dropwise while keeping the temperature at below −10° C. and then N-Iodosuccinimide (NIS) (7.76 g, 34.5 mmol) was added in three portions. The resulted mixture was stirred for 4 hours at −5° C. and for an additional 30 min. at room temperature. Then the reaction mixture was diluted with Dichloromethane, filtered through Celite, stirred for 30 min with saturated aq. Sodium Hydrogen Carbonate solution (300 mL) and the aqueous layer was separated. The organic layer was washed twice with 300 mL portions of Sodium Thiosulfate saturated aqueous solution and water. The combined aqueous solution was washed with 300 mL of Dichloromethane. The combined organic solution was dried over anhydrous Sodium Sulfate, filtered and evaporated under reduced pressure. After filtration through a short Silica Gel column 12.7 g (70%) of the desired compound [8] was obtained.

Hydrolysis of the compound [8] according to the standard procedure afforded 4.2 g (56.5% yield) of M6G.

EXAMPLE 2–12

The procedure of Example 1 was performed with Thioglycoside [11] and Morphine derivative [3a]. The results are shown in Table 1.

TABLE 1

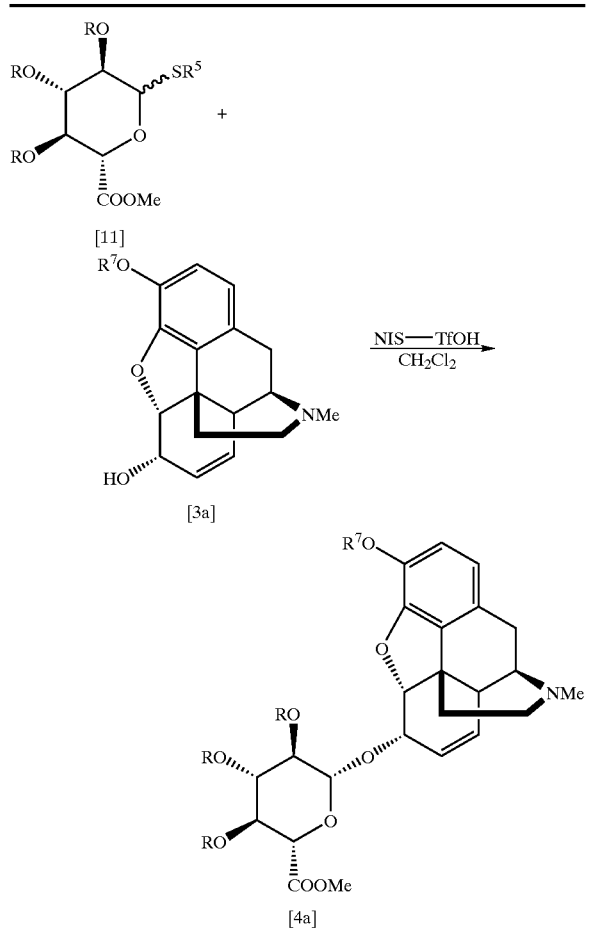

| Ex. No. | R | $R^7$ | $R^5$ | T, ° C. | α/β | Yield, % |
|---|---|---|---|---|---|---|
| 2 | Ac | Ac | Et | −15 | 1:7 | 20 |
| 3 | Ac | Ac | Et | −15 | 1:6 | 17 |
| 4 | Ac | Ac | Et | −40 | 1:9 | 21 |
| 5 | Bz | Ac | Et | −23 | 1:10 | 40 |
| 6 | Bz | Bz | Et | −23 | 1:10 | 62 |
| 7 | Bz | Bz | Ph | −10 | 1:9 | 70 |
| 8 | Bz | Bz | Ph | −15 | 1:16 | 65 |
| 9 | Bz | Bz | Ph | −23 | 1:25 | 71 |
| 10 | Pr$^i$CO | Bz | Ph | −10 | 1:18 | 75 |
| 11 | Pr$^i$CO | MeOCO | Ph | −25 | 1:37 | 70 |
| 12 | Pr$^i$CO | Bz | Ph | −23 | 1:22 | 47 |

EXAMPLE 13

Preparation of Methyl (3-O-Acetylmorphin-6-yl-2', 3',4'-Tri-O-benzoyl-β-D-glucopyranosid)uronate of Formula [13]

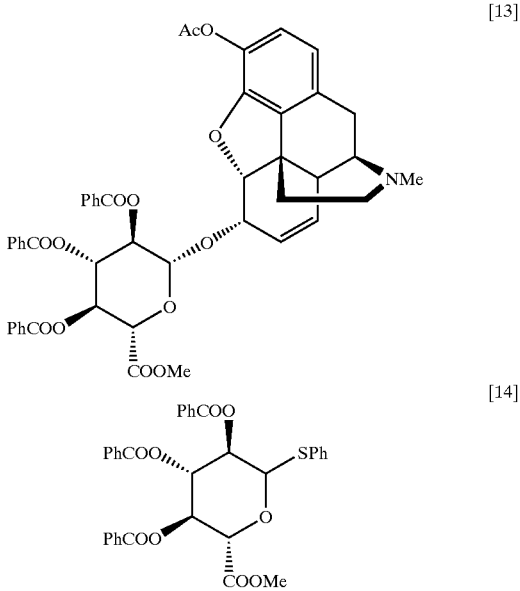

A suspension of 4.2 g (6.9 mmol) of Thioglycoside [14], 1.5 g (4.6 mmol) of freshly prepared, vacuum-dried 3-O-Acetylmorphine and 6.0 g 3 Å Molecular Sieves in 60 mL Dichloromethane was stirred at room temperature for 30 min and cooled to −15° C. by an ice-salt-acetone bath. Trifluoromethanesulfonic acid (TfOH) (1.0 g, 6.7 mmol) was added dropwise while keeping the temperature at below −10° C. and then N-Iodosuccinimide (NIS) (1.55 g, 6.9 mmol) was added in three portions. The resulted mixture was stirred for 4 hours at −5° C. and for an additional 30 min. at room temperature. Then the reaction mixture was diluted with Dichloromethane, filtered through Celite, stirred for 30 min with saturated aq. Sodium Hydrogen Carbonate solution (60 mL) and the aqueous layer was separated. The organic layer was washed twice with 60 mL portions of Sodium Thiosulphate saturated aqueous solution and water. The combined aqueous solution was washed with 60 mL of Dichloromethane. Combined organic solution was dried over Sodium Sulfate anhydrous, filtered and evaporated under reduced pressure. After separation on Silica Gel collumn compound [13] 1.93 g (51%) and 0.4 g of Morphine were obtained.

EXAMPLE 14

The procedure of Example 13 was performed with Thioglycoside [15] and resulted in a 1:2 mixture of compound [17] and di-O-acetylmorphine.

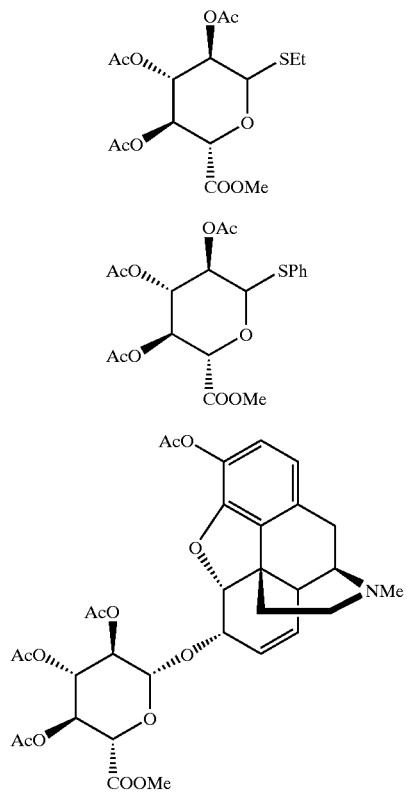

[15]

[16]

[17]

EXAMPLE 15

In an analogous manner the procedure of Example 1 was performed with Thioglycoside [16], resulting in a 2:1 mixture of compound [17] and di-O-acetylmorphine.

EXAMPLE 16

A solution of 5 Methyl(ethyl-2,3,4-tri-O-acetyl-1-thioglucopyran)uronate [18] in 50 mL Dichloroethane was charged under Argon into a round bottom flask, equipped with a magnetic stirrer and thermocouple and colled to −5° C. Molecular sieved 5 Å° (5 g) were added and the stirring was started. A solution of 3-Acetylmorphine [19] (2.88 g) in 20 mL Dichloroethane was added, followed by Trifluoromethanesulfonic acid (1.98 g). Temperature of the reaction mixture was allowed to reach −2° C. Then, the suspension of N-iodosuccinimide (2.97 g) in 20 mL Dichloroethane and 30 mL Dietyl ether was added. The reaction mixture became black and was stirred at −4° C. . . . 0° C. for an additional 2 hours. The solution was diluted with 80 mL of Dichloroethane, washed consistently with sodium bicarbonate solution, sodium bisulphate solution (20 g in 200 mL) and water. The organic layer became light yellow. After separation the organic layer was dried over sodium sulphate and concentrated under reduced pressure. The obtained ester was hydrolysed and Morphine-6-β-D-glucuronide (M6G) was separated and purified according to the published procedure. $^1$H NMR (D$_2$O) conforms to structure.

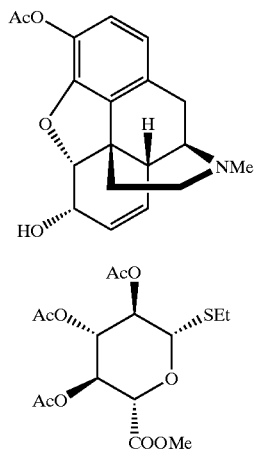

[19]

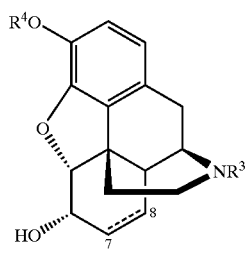

[18]

REFERENCES

1. Osborne, R., et al., The Lancet, 1988, 828
2. Osborne, R., et al., Br. J. Clin. Pharm. 1992, v. 34, 130
3. Frances, B;, et al., J. Pharm. Exp. Ther., 1992, v. 262, 25

What is claimed is:

1. A process for glycosidation of a 4,5-Epoxymorphinan-6-ol, or a salt or complex thereof, comprising reacting said 4,5-Epoxymorphinan-6-ol, or a salt or complex thereof, with a thioglycoside.

2. The process according to claim 1, wherein said 4,5-Epoxymorphinan-6-ol is selected from compounds of formula [3]:

[3]

wherein:

said ----- bond between 7 and 8 is either olefin or dihydro adduct;

$R^3$ is alkyl, arylmethyl, allyl, cyclopropylmethyl, cyclobutylmethyl, hydrogen, acyl, alkoxycarbonyl, aralkoxycarbonyl, haloalkoxycarbonyl, vinyloxycarbonyl, or allyloxycarbonyl; and $R^4$ is alkyl, arylmethyl, 2-(4-morpholinyl)ethyl, acyl, alkoxycarbonyl, aralkoxycarbonyl, haloalkoxycarbonyl, vinyloxycarbonyl, or allyloxycarbonyl.

3. The process according to claim 1, wherein said 4,5-Epoxymorphinan-6-ol is 3-O-Acylmorphine, 3-O-Acylnormorphine, 3-O-Acylnalbuphine, 3-O-Acylnalmorphine, 3-O-Acyldihydromorphine, 3-O-Benzylmorphine, 3-O-Benzyldihydromorphine, N,O$^3$-Dibenzylnormorphine, Codeine, Ethylmorphine, Dihydrocodeine, Pholcodine, 3-O-Alkoxycarbonylmorphine, 3-O-Benzyloxycarbonylmorphine, or N,O$^3$-Bis(benzyloxycarbonyl)normorphine.

4. The process according to claim 1, wherein said thioglycoside is selected from compounds of formula [2]:

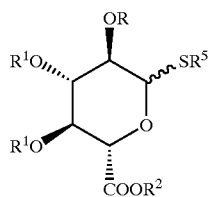

wherein:
R is acyl, alkoxycarbonyl, aralkoxycarbonyl, haloalkoxycarbonyl, vinyloxycarbonyl, or allyloxycarbonyl;
$R^1$ is alkyl, arylmethyl, acyl, alkoxycarbonyl, aralkoxycarbonyl, haloalkoxycarbonyl, vinyloxycarbonyl, or allyloxycarbonyl;
$R^2$ is alkyl, haloalkyl, or aralkyl; and
$R^5$ is alkyl or aryl.

5. The process according to claim 1, wherein said thioglycoside is selected from compounds of formula [12]:

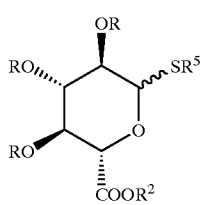

wherein:
R is acyl, alkoxycarbonyl, aralkoxycarbonyl, haloalkoxycarbonyl,
vinyloxycarbonyl, or allyloxycarbonyl;
$R^2$ is alkyl, haloalkyl, or aralkyl; and
$R^5$ is alkyl or aryl.

6. The process according to claim 1, wherein said thioglycoside is selected from compounds of formula [11]:

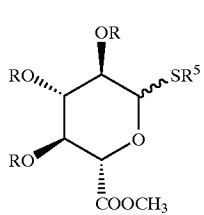

wherein:
R is acyl, alkoxycarbonyl, aralkoxycarbonyl, haloalkoxycarbonyl, vinyloxycarbonyl, or allyloxycarbonyl; and
$R^5$ is alkyl or aryl.

7. The process according to claim 1, wherein said reacting is performed in the presence of a thiophilic promoter.

8. The process according to claim 7, wherein said thiophilic promoter is a halonium ion source, Dimethyl (methylthio)sulfonium triflate, Dimethyl(methylthio)sulfonium tetrafluoroborate, methyl triflate, or methylfluorosulfonate.

9. The process according to claim 7, wherein said halonium ion source is a mixture of N-halosuccinimide and an acid or iodonium dicollidine perchlorate (IDCP).

10. The process according to claim 9, wherein said N-halosuccinimide is N-iodosuccinimide (NIS) or N-bromosuccinimide (NBS).

11. The process according to claim 9, wherein said acid is triflic acid, trimethylsilyl triflate, silver triflate, silver tetrafluoroborate, or trifluoromethanesulfonic acid.

12. The process according to claim 1, wherein said reacting is performed in the presence of a molecular sieve.

13. The process according to claim 1, wherein said reacting is performed in a reaction-inert solvent.

14. The process according to claim 13, wherein said solvent comprises at least one non-protic, reaction-inert solvent, wherein said solvent is dichloromethane, chloroform, 1,2-dichloroethane, ether, acetonitrile, diethyl ether, or ethyl acetate.

15. A process for glycosidation of a 4,5-Epoxymorphinan-6-ol, or a salt or complex thereof, comprising reacting a 4,5-Epoxymorphinan-6-ol selected from compounds of formula [3]:

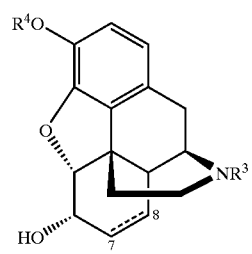

wherein:
said ----- bond between 7 and 8 is either olefin or dihydro adduct;
$R^3$ is alkyl, arylmethyl, allyl, cyclopropylmethyl, cyclobutylmethyl, hydrogen, acyl, alkoxycarbonyl, aralkoxycarbonyl, haloalkoxycarbonyl, vinyloxycarbonyl, or allyloxycarbonyl; and
$R^4$ is alkyl, arylmethyl, 2-(4-morpholinyl)ethyl, acyl, alkoxycarbonyl, aralkoxycarbonyl, haloalkoxycarbonyl, vinyloxycarbonyl, or allyloxycarbonyl;
with a glycoside donor selected from thioglycosides of formula [2]:

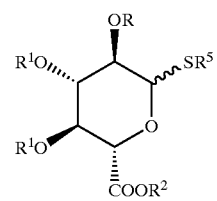

wherein:
R is acyl, alkoxycarbonyl, aralkoxycarbonyl, haloalkoxycarbonyl, vinyloxycarbonyl, or allyloxycarbonyl;
$R^1$ is alkyl, arylmethyl, acyl, alkoxycarbonyl, aralkoxycarbonyl, haloalkoxycarbonyl, vinyloxycarbonyl, or allyloxycarbonyl;
$R^2$ is alkyl, haloalkyl, or aralkyl; and
$R^5$ is alkyl or aryl; and
wherein said reacting is performed under conditions capable of forming a protected 4,5-Epoxymorphinan-6-β-D-glucuronide of formula [1], or a salt or complex thereof:

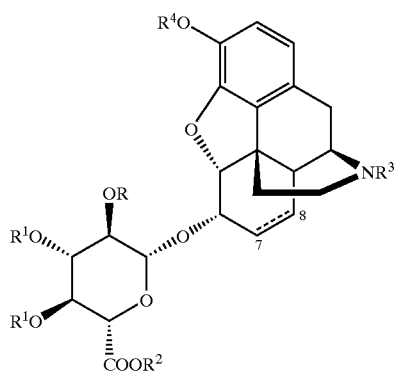

wherein:

said ----- bond between 7 and 8 is either olefin or dihydro adduct;

R is acyl, alkoxycarbonyl, aralkoxycarbonyl, haloalkoxycarbonyl, vinyloxycarbonyl, or allyloxycarbonyl;

$R^1$ is alkyl, arylmethyl, acyl, alkoxycarbonyl, aralkoxycarbonyl, haloalkoxycarbonyl, vinyloxycarbonyl, or allyloxycarbonyl;

$R^2$ is alkyl, haloalkyl, or aralkyl;

$R^3$ is alkyl, arylmethyl, allyl, cyclopropylmethyl, cyclobutylmethyl, hydrogen, acyl, alkoxycarbonyl, aralkoxycarbonyl, haloalkoxycarbonyl, vinyloxycarbonyl, or allyloxycarbonyl; and $R^4$ is alkyl, arylmethyl, 2-(4-morpholinyl)ethyl, acyl, alkoxycarbonyl, aralkoxycarbonyl, haloalkoxycarbonyl, vinyloxycarbonyl, or allyloxycarbonyl.

16. A protected 4,5-Epoxymorphinan-6-β-D-glucuronide of formula [1], or a salt or complex thereof:

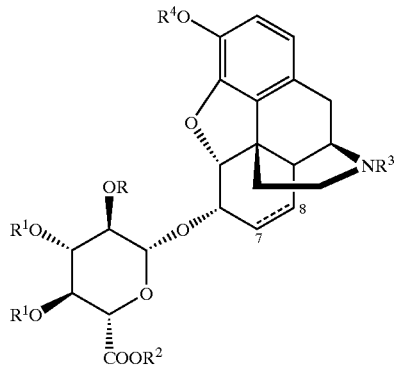

wherein:

said ----- bond between 7 and 8 is either olefin or dihydro adduct;

R is acyl, alkoxycarbonyl, aralkoxycarbonyl, haloalkoxycarbonyl, vinyloxycarbonyl, or allyloxycarbonyl;

$R^1$ is alkyl, arylmethyl, acyl, alkoxycarbonyl, aralkoxycarbonyl, haloalkoxycarbonyl, vinyloxycarbonyl, or allyloxycarbonyl;

$R^2$ is alkyl, haloalkyl, or aralkyl;

$R^3$ is alkyl, arylmethyl, allyl, cyclopropylmethyl, cyclobutylmethyl, hydrogen, acyl, alkoxycarbonyl, aralkoxycarbonyl, haloalkoxycarbonyl, vinyloxycarbonyl, or allyloxycarbonyl; and $R^4$ is alkyl, arylmethyl, 2-(4-morpholinyl)ethyl, acyl, alkoxycarbonyl, aralkoxycarbonyl, haloalkoxycarbonyl, vinyloxycarbonyl, or allyloxycarbonyl, and provided that:
(1) when R and $R^1$ are isobutyryl and $R^2$ is methyl, then $R^4$ is not acetyl, benzoyl, isobutyryl, or pivalyl,
(2) when R and $R^1$ are pivalyl and $R^2$ is methyl, then $R^4$ is not pivalyl,
(3) the protected 4,5-Epoxymorphinan-6-β-D-glucuronide is not the chlorohydrate hemihydrate of [acetyl-3 (triacetyl-2,3,4-β-D-glucopyranoside)-6 yl-6 morphine] methyl uronate, and
(4) the protected 4,5-Epoxymorphinan-6-β-D-glucuronide is not:

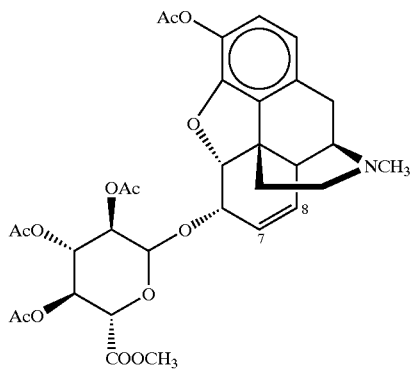

wherein Ac is acetyl.

17. A process for preparing Morphine-6-β-D-glucuronide (M6G), comprising:

(i) reacting a 4,5-Epoxymorphinan-6-ol, or a salt or complex thereof, with a thioglycoside to prepare a protected 4,5-Epoxymorphinan-6-β-D-glucuronide; and (ii) hydrolyzing said protected 4,5-Epoxymorphinan-6-β-D-glucuronide to prepare Morphine-6-β-D-glucuronide (M6G).

18. A process for preparing Morphine-6-β-D-glucuronide (M6G) comprising:

(i) reacting a 4,5-Epoxymorphinan-6-ol selected from compounds of formula [3]:

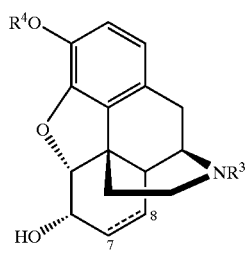

wherein:

said ----- bond between 7 and 8 is either olefin or dihydro adduct;

R³ is alkyl, arylmethyl, allyl, cyclopropylmethyl, cyclobutylmethyl, hydrogen, acyl, alkoxycarbonyl, aralkoxycarbonyl, haloalkoxycarbonyl, vinyloxycarbonyl, or allyloxycarbonyl; and R⁴ is alkyl, arylmethyl, 2-(4-morpholinyl)ethyl, acyl, alkoxycarbonyl, aralkoxycarbonyl, haloalkoxycarbonyl, vinyloxycarbonyl, or allyloxycarbonyl;

with a glycoside donor selected from thioglycosides of formula [2]:

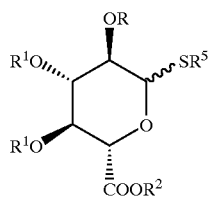

[2]

wherein:

R is acyl, alkoxycarbonyl, aralkoxycarbonyl, haloalkoxycarbonyl, vinyloxycarbonyl, or allyloxycarbonyl;

R¹ is alkyl, arylmethyl, acyl, alkoxycarbonyl, aralkoxycarbonyl, haloalkoxycarbonyl, vinyloxycarbonyl, or allyloxycarbonyl;

R² is alkyl, haloalkyl, or aralkyl; and

R⁵ is alkyl or aryl; and wherein said reacting is performed under conditions capable of forming a protected 4,5-Epoxymorphinan-6-β-D-glucuronide of formula [1], or a salt or complex thereof:

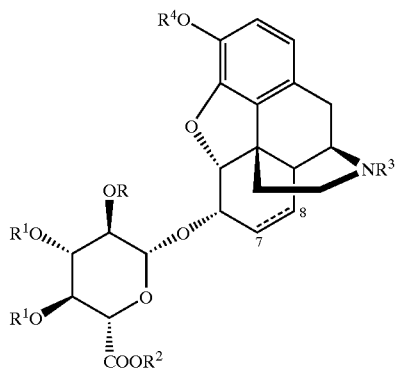

[1]

wherein:
said ----- bond between 7 and 8 is either olefin or dihydro adduct;

R is acyl, alkoxycarbonyl, aralkoxycarbonyl, haloalkoxycarbonyl, vinyloxycarbonyl, or allyloxycarbonyl;

R¹ is alkyl, arylmethyl, acyl, alkoxycarbonyl, aralkoxycarbonyl, haloalkoxycarbonyl, vinyloxycarbonyl, or allyloxycarbonyl;

R² is alkyl, haloalkyl, or aralkyl;

R³ is alkyl, arylmethyl, allyl, cyclopropylmethyl, cyclobutylmethyl, hydrogen, acyl, alkoxycarbonyl, aralkoxycarbonyl, haloalkoxycarbonyl, vinyloxycarbonyl, or allyloxycarbonyl; and R⁴ is alkyl, arylmethyl, 2-(4-morpholinyl)ethyl, acyl, alkoxycarbonyl, aralkoxycarbonyl, haloalkoxycarbonyl, vinyloxycarbonyl, or allyloxycarbonyl; and (ii) hydrolyzing said protected 4,5-Epoxymorphinan-6-β-D-glucuronide to prepare Morphine6-β-D-glucuronide (M6G).

* * * * *